United States Patent [19]

Mills et al.

[11] Patent Number: 5,394,891
[45] Date of Patent: Mar. 7, 1995

[54] SURGICAL DRAPE WITH IMPROVED CRITICAL ZONE PANEL

[75] Inventors: Veronica A. Mills, Cincinnati; Jeffrey L. Tayor, Wyoming, both of Ohio

[73] Assignee: Standard Textile Company, Inc., Cincinnati, Ohio

[21] Appl. No.: 85,011

[22] Filed: Jun. 29, 1993

Related U.S. Application Data

[63] Continuation-in-part of Ser. No. 680,089, Apr. 3, 1991, Pat. No. 5,222,507.

[51] Int. Cl.⁶ .............................................. A61F 13/00
[52] U.S. Cl. .................................... 128/852; 128/853; 128/649
[58] Field of Search ............... 128/846, 849, 850, 851, 128/852, 853, 854, 855, 856; 428/265, 266

[56] References Cited

U.S. PATENT DOCUMENTS

| | | | |
|---|---|---|---|
| Re. 27,710 | 7/1973 | Melges | 128/853 X |
| 4,040,418 | 8/1977 | Collins | 128/852 |
| 4,275,720 | 6/1981 | Wichman | 128/853 |
| 4,323,062 | 4/1982 | Canty | 128/852 |
| 4,561,434 | 12/1985 | Taylor | 128/849 |
| 4,569,341 | 2/1986 | Morris | 128/853 |
| 4,586,498 | 5/1986 | Morris | 128/853 |
| 4,616,692 | 10/1986 | Martin et al. | 604/356 X |
| 4,957,120 | 9/1990 | Grier-Idris | 128/849 |
| 5,010,899 | 4/1991 | Thompson | 128/849 |

Primary Examiner—Sam Rimell
Attorney, Agent, or Firm—Kinney & Schenk

[57] ABSTRACT

A fenestrated surgical drape includes a "critical zone" panel surrounding the fenestration. The "critical zone" panel comprises an upper absorbent panel and underlying, upper and lower barrier panels. The absorbent layer and upper barrier panel are joined as a first sub-assembly. The lower barrier panel and the main panel of the drape are joined as a second sub-assembly. The sub-assemblies are joined by stitching marginally of the fenestration. The first sub-assembly is then joined to the lower barrier panel by stitching marginally of its outer periphery. The marginal edge portions of the "critical zone" panel are folded inwardly to form liquid receiving troughs along the side and end edges of the "critical zone" panel. These troughs intersect at the corners of the "critical zone" panel. Further folded portions of the "critical zone" panel close the intersecting ends of the troughs. Snap fastener elements hold the marginal portions of the "critical zone" in these folded relations. The snap fastener elements are releasable to facilitate laundering of the surgical drape. Tube loops are provided for releasably holding electrical instruments employed in a surgical procedure. The construction of the tube loops protects a patient against electrical shock and/or burns.

31 Claims, 9 Drawing Sheets

SURGICAL DRAPE WITH IMPROVED CRITICAL ZONE PANEL

The present invention is a continuation-in-part application of the prior application of one of the applicants in the present invention, said prior application being identified as Ser. No. 680,089, filed Apr. 3, 1991, U.S. Pat. No. 5,222,507, which application is of common assignment with the present application.

The present invention relates to improvements in surgical drapes.

In the performance of surgical procedures, it is a customary and usual practice to limit the extent to which body liquids, or fluids used in the procedure, will come into contact with the skin surfaces of the patient. One of the reasons for this practice is based on the theory that micro-organisms migrate through a liquid medium instantaneously. Therefore, if there are any micro-organisms on the skin surface of the patent, a surgical drape inhibits their transfer to the surgical site.

To limit the spread of micro-organisms, clothes are draped over the patient so that only the area immediately adjacent to the area of the surgical site is exposed. The clothes, or surgical drapes, as they are generally designated, limit contact between the skin surface and blood, or other body liquid, which might exude from an incision. Surgical drapes also limit the extent to which liquids, employed in a procedure, contact the skin surface of a patient.

The use of surgical drapes is more than a matter of general cleanliness and comfort, since microorganisms on the skin of the patient can be the source of infection.

The present invention is, more specifically, directed to improvements in fenestrated, surgical drapes. This type of is provided with a fenestration, usually within the outline of the drape, though sometimes opening from a side of the drape. The fenestration is registered with the site of the surgical procedure. The area and shape of the fenestration is such as to minimize the area of the patient's skin that is exposed by the fenestra, consistent with the nature of the procedure to be performed. There are a wide variety of fenestrated, surgical drapes, which are specifically designed for use in the performance of various surgical procedures.

As indicated, the general purpose of a surgical drape is to minimize the area of a patient's person that is directly exposed to contact with liquids, including body fluids, that are incident to the performance of a surgical procedure. In some cases there can be substantial quantities of body fluids that emanate from the surgical site. The area marginally of a fenestration (i.e., immediately adjacent and within a foot or so of the fenestration) is referenced as a "critical zone", due to the large amount of body fluids and other liquids that can be found in this region. To guard against such liquids penetrating (striking through) the drape and possibly contaminating the underlying portion of the patient's person, it has been an accepted practice to provide a "critical zone" panel, which overlays the main panel of the drape and provides additional barrier protection for preventing such liquids from striking through to the patient's person.

During the performance of a surgical procedure, the amount of body liquids and other liquids incident to the performance of the procedure can be so great that they spill, from the area or the fenestration and the "critical zone" panel, and fall onto the operating room floor. Such spillage creates a hazard in that possibly infectious microorganisms are spread from the surgical site, making their containment more difficult. Further, the liquids could cause a doctor or operating room assistant to slip and fall. This could cause injury to the person falling, as well as jeopardizing the well being of the patient.

In many types of surgical procedures, the volume of liquids incident to the procedure is relatively small. This, plus the position of the patient on the operating table and the configuration of the surgical drape for such procedure, all contribute to an ability to control liquids, i.e., to prevent their spilling to the floor, through the provision of troughs on opposite sides of the critical zone panel of the drape. However, in other procedures, exemplified by a Cesarian section delivery, the amount of liquids involved, is relatively large. This plus the fact that the abdomen of the patient protrudes upwardly leads to liquids flowing toward one end or the other of the drape. Such liquids flow from the end portions of the critical zone panel and then strike through the main panel of the drape and can also fall from the drape, creating the hazardous conditions discussed above.

At this point, it will be further noted that there are two primary classifications of surgical drapes, one being disposable and the other being reusable.

Disposable surgical drapes are generally formed of non-woven fibers and, as the name implies, are simply discarded after a single use. Disposable drapes are relatively inexpensive, but their disposal has become a problem of progressively increasing seriousness, as their potential for pollution of the environment becomes better recognized.

Reusable surgical drapes, as that name also implies, are laundered (washed and dried) and sterilized after each use, so that they may be employed several times. Reusable surgical drapes are, generally, constructed of woven or knit fabrics, which have a "hand", or tactile handling characteristic that facilitates their use and is preferred by medical professionals. The acquisition cost of reusable surgical drapes is higher than that of their disposable counterparts. However, including the costs of washing and sterilization, the per use cost of reusable surgical drapes can be substantially less than that of functionally equivalent disposable drapes.

Accordingly, a primary object of the present invention is to provide a reusable surgical drape, adapted to be used in surgical procedures involving large volumes of liquids.

A further and related object of the present invention is to attain the above end and further to provide a drape which maintains such liquids within the confines of the critical zone panel.

A related end sought by the foregoing objects is to decrease the exposure of operating room personnel to possibly infections liquids by physically containing such liquids so that they will not spill to the floor and splatter, or other wise become airborne, or so spread that the exposure to infectious microorganisms is increased.

Yet another object of the present invention is to provide a surgical drape that attains the foregoing ends and is, additionally, to achieve these ends by a simplified construction that has the necessary ruggedness for multiple uses and multiple laundering/sterilization cycles.

The foregoing ends may, in accordance with one of the broader aspects of the invention, be attained by a reusable, surgical drape adapted to overlie a patient during the performance of a surgical procedure and having a fenestration for registration with the site of the surgical procedure. This drape is constructed of launderable/sterilizable fabric panels, which comprise a main panel and a "critical zone" panel, of lesser lateral extent, extending outwardly from the fenestration.

A marginal edge portion of the "critical zone" panel is folded on itself to define an upwardly open trough for capturing liquids that are incident to the performance of a surgical procedure. Releasable means secure the folded portion of the "critical zone" panel to the underlying main portion so that the folded portion may be released to facilitate laundering of the drape.

This drape is further characterized in that the "critical zone" panel comprises an upper barrier panel, and a lower barrier panel. The upper barrier panel is joined to the main panel only by stitching marginally of the fenestration, and the upper barrier panel is joined to the lower barrier panel by stitching marginally of their outer peripheries.

The foregoing ends may, in accordance with other of the broader aspects of the invention, be attained by a reusable, surgical drape adapted to overlie a patient during the performance of a surgical procedure and having a fenestration for registration with the site of a surgical procedure, as generally characterized above.

One or more of the marginal edge portions of the "critical zone" panel are folded inwardly to form troughs. These portions are releasably secured in folded relation to permit folded portions to be released during laundering, so as to facilitate that operation. Snap fastener elements, employed for this purpose, are mounted in a fashion that preserves the barrier properties of the lower barrier panel of the "critical zone" panel.

In accordance with the method aspects of the invention the lower barrier panel is secured to the main panel of the drape, by stitching marginally of the fenestration. Snap fastener elements employed in securing the marginal portion of the "critical zone" panel in folded relation, are mounted in the upper barrier panel inwardly of a given edge thereof. The outer peripheries of the upper and lower barrier panels are then joined by stitching. Second, snap fastener elements are then mounted in both barrier panels along the given edge in a position to cooperate with the first snap fastener elements.

In attaining other ends of the invention, as related to dealing with large quantities of liquids during the performance of a surgical procedure, the drape may be constructed of launderable/sterilizable fabric panels. The drape comprises a main panel and a "critical zone" panel, of lesser lateral extent, extending outwardly from the fenestration. The "critical zone" panel comprises a liquid repellant, barrier panel.

A side marginal edge portion of the barrier panel is folded on itself to define an upwardly open, side trough, for the reception therein of liquids incident to the performance of a surgical procedure. An end marginal edge portion of the barrier panel is folded on itself to define an upwardly open, end trough, for the reception therein of liquids incident to the performance of a surgical procedure. The end and side 1roughs intersect at a corner of the "critical zone" panel. Means are provided for releasably securing the folded, marginal edge portions of the barrier panel to the main portion of the barrier panel.

This drape is further characterized by releasable means for securing the folded side and end marginal edge portions, at the corner of the "critical zone" panel, in further folded relation to close the intersecting ends of the troughs.

The troughs may be formed along both side edges and one or both of the end edges of the "critical zone" panel, so that there will be intersecting ends of the troughs at a plurality of corners of the "critical zone" panel. The described construction, for closing the ends of the troughs would be used at each corner where there is an intersection of a side and an end trough.

Certain surgical procedures involve the use of electrically energized instruments, as for cauterization. In the use of such electrical instruments it is a common practice to releasably position them by a strap like device that is referenced as a "tube loop".

In brief, a tube loop comprises a fabric strap that has a free end that is wrapped around an electrical instrument and secured in this holding position by snap fastening elements. While metallic snap fastening elements are preferred, they pose a possible hazard for the surgical patient.

This is to say that the possibility exists that some malfunction of the instrument could cause the casing of the instrument to become electrically charged. In such case, if the metalic snap fastener elements of the tube loop were in contact with the electrically charged instrument, the snap fastener elements would likewise be electrically charged. Thus, any contact between the snap fasteners and the patient, or any close proximity of the snap fasteners with the patient could result in the patient's being shocked and/or burned.

It is, therefore, yet a further object of the present invention to minimize, if not eliminate, the possibility a patient being electrically shocked and/or burned as a result of the metallic snap fastener elements of a tube loop becoming electrically charged.

This last end is obtained through a reusable, surgical drape that includes a tube loop for releasably holding an electrical instrument. The loop comprises an endless loop formed of fabric. The fabric loop is flattened to form a strap comprised of an upper fabric ply and a lower fabric ply.

One end portion of the strap is secured to the drape, leaving the remainder of the strap as a free end portion. A first, metallic snap fastener element is mounted on the free end portion of the strap. A second, metallic snap fastener element is mounted on the secured end portion of the strap and adapted to be engaged by the first snap fastener element in holding an electrical instrument.

The tube loop is characterized in that the second snap fastener element is mounted onto the upper fabric ply and the lower fabric ply is disposed between the second snap fastener element and the drape to thereby space the snap fastener elements from a patient upon whom the drape has been positioned and thus protect the patient from an electrical shock and/or burn.

The first snap fastener element is, preferably mounted on both the upper and lower plies of the strap.

The endless fabric loop may be formed of a length of woven tape, the ends of which are joined by a first stitching. The joined ends of the length of tape may be disposed in the upper ply of the strap, and the one end portion of the strap may be secured to the surgical drape by second stitching disposed between the second snap fastener element and the outer end of the secured portion of the strap. Further, third stitching disposed intermediate the length of the strap may also be employed in securing the one end portion of the strap to the surgical drape.

The above and other related objects and features of the invention will be apparent from a reading of a pre-

Figure 1:
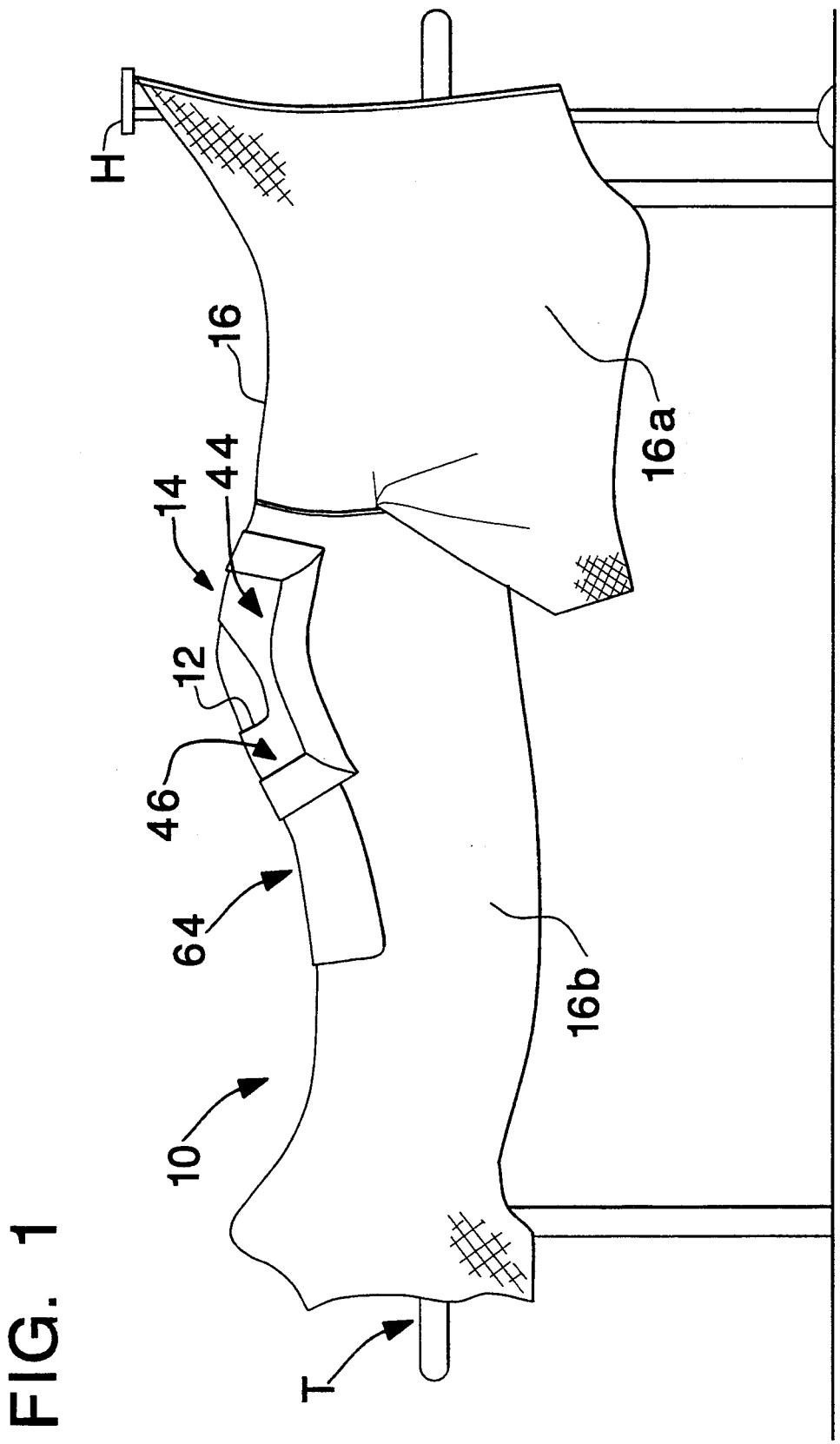
FIG. 1 is an elevation illustrating the surgical drape of the present invention deployed on a patient who is positioned on an operating table.

Reference is first made to FIG. 1, which illustrates the present surgical drape, indicated generally by reference character 10, deployed upon a patient positioned, on an operating table T, for delivery of an baby by Cesarian section. The drape 10 is held in spaced relation above the head of the patient by a holder H to provide access to the patient's head by the anesthesiologist.

The drape 10 includes a fenestration (opening) 12, which is registered with the site of the surgical procedure. As illustrated in FIG. 1, this would be in the area of the patient's abdomen. The fenestration 12 is within the confines of a "critical zone" panel 14, which, in turn, is disposed generally centrally of the main panel 16 of the drape 10.

Figure 2:
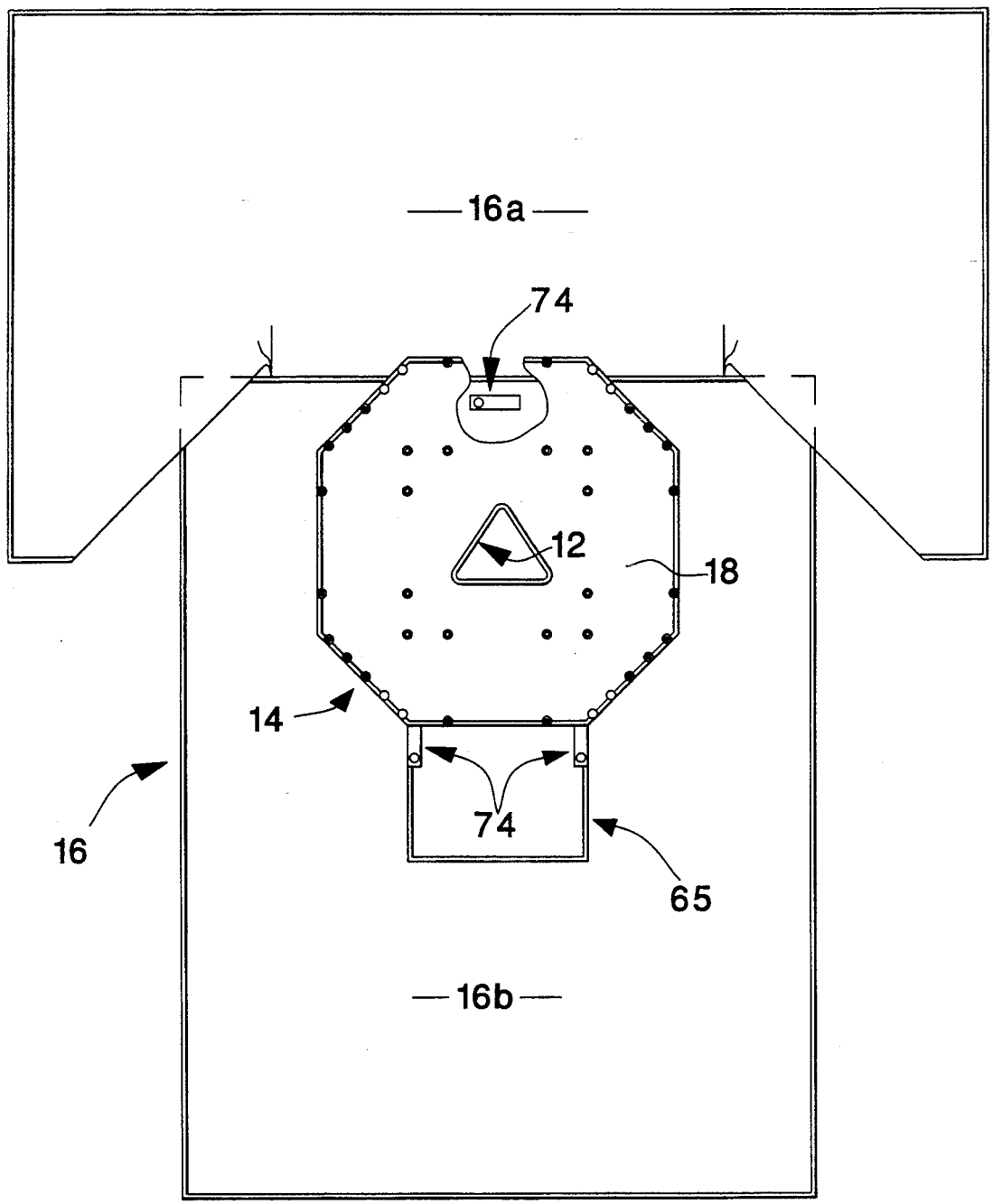
FIG. 2 is a plan view of the surgical drape seen in FIG. 1.
Figure 3:
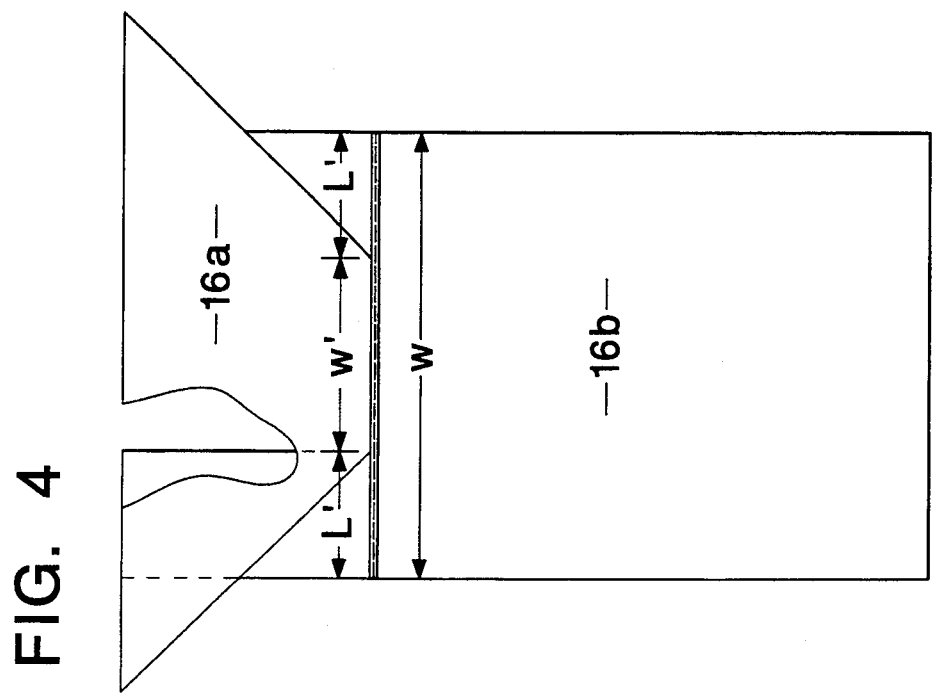
FIG. 3 is a plan view of the component panels of a main panel, before being joined.
Figure 4:
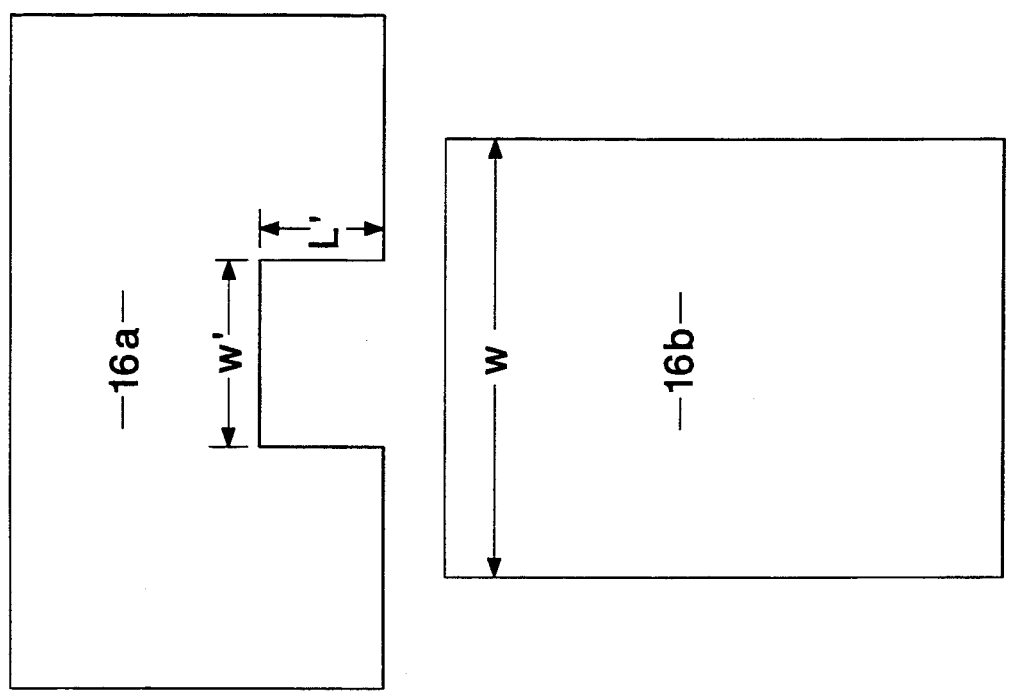
FIG. 4 is a plan view of the component panels of the main panel, after being joined.

Reference is next made to FIGS. 2–4 which better illustrate that the main panel 16, of the drape 10, is compositely formed by panels 16a and 16b, which are appropriately joined by stitching. The outline of the main panel 16 is edge bound by a binding tape 17, in conventional fashion. The panels 16a and 16b are both rectangular. The panel 16b has a width dimension w. The panel 16a has a rectangular recess, centrally of one widthwise edge. The recess has a widthwise dimension w' and a lengthwise dimension l'. The periphery of the recess (w' plus twice the distance l') equals the width w of the panel 16b. The panel 16a and 16b are joined by stitching the recess periphery to the edge w.

The described manner of joining the panels 16a and 16b causes a folding of the marginal edge portions of the panels 16a, 16b, at their juncture, which facilitates deployment of the drape on a patient.

The main panel 16 is preferably formed of a woven fabric which has characteristics that make it particularly effective in protecting the patient during a surgical procedure.

Thus, the material of main panel 12 is highly flexible with a relatively light weight, in the order of 4.0 ounce per square yard. The flexible characteristic facilitates the drape 10 to conform to the contour of a person's body so that the fenestration 12 may be readily placed over the surgical site, and then remain in registration with the surgical site as the surgical procedure is performed. The light weight characteristic, among other things, means a lower volume, or mass, for the surgical drape, which minimizes the volume requirements for washing, sterilizing and storage shelf space.

Another characteristic of the fabric for panel 16 is that it has a relatively high coefficient of friction. This characteristic further assists in preventing the drape from inadvertently shifting relative to the body of the patient, to the end that the fenestration 12 is maintained in registration with the site of the incision.

A preferred fabric for the main panel 16 is described in copending U.S. patent application Ser. No. 860,315, filed Mar. 30, 1992, in the names of Jeffrey L. Taylor, John M. Smith and C. Dean Goad. Briefly this fabric may be characterized as a synthetic yarn fabric having a "hand" which is essentially the same as the "hand" of cotton muslin. This synthetic yarn fabric provides several advantages over cotton muslin, as well as percale fabric, both of which have been used in fabricating reusable surgical drapes. "Hand" includes the flexibility of the fabric, which facilitates its ability to be draped over and conform to the contours of a patient.

These advantages include non-linting and non-pilling, which eliminate a potential source of contamination in the operating arena.

The preferred fabric is further characterized in that it is woven with a weave which creates floats and by the floats comprising air texturized, core and effect, polyester yarns. More specifically, it is preferred that the main panel fabric be a two by two twill in which the filling yarns are air texturized, core and effect yarns and the warp yarns are false twist texturized yarns, both of the warp yarns and filling yarns are set yarns to provide dimensional stability.

The described fabric construction, and particularly the air texturized, core and effect yarn provides the desired coefficient of friction for the main panel 16. It is to be noted that coefficient of friction is also a factor, or characteristic, of the desired "hand" of the main panel 16, such characteristic being gauged against cotton muslin.

It is further preferred that the main panel be liquid repellant. This means that water or other liquids will not readily penetrate the fabric, but, nonetheless the fabric does not provide a barrier function of resisting liquid penetration by liquid having any substantial measure of hydrostatic head. Polyester (or equivalent synthetic materials, such as nylon) are hydrophobic. This hydrophobic property provides inherent water repellency. Additionally, the above referenced application provides teachings of the use of finish treatments which enhance the water repellency of the fabric.

Further characteristics of the fabric of panel 16 are that it has a relatively high strength, it creates little or no lint, either in use or in washing, and that its functionally characteristics are not unduly degraded by repeated laundering/sterilization cycles. These characteristics contribute to a lower cost of the present surgical drape, on a per use basis, even though its acquisition cost may exceed that of conventional reusable surgical drapes.

Figure 5:
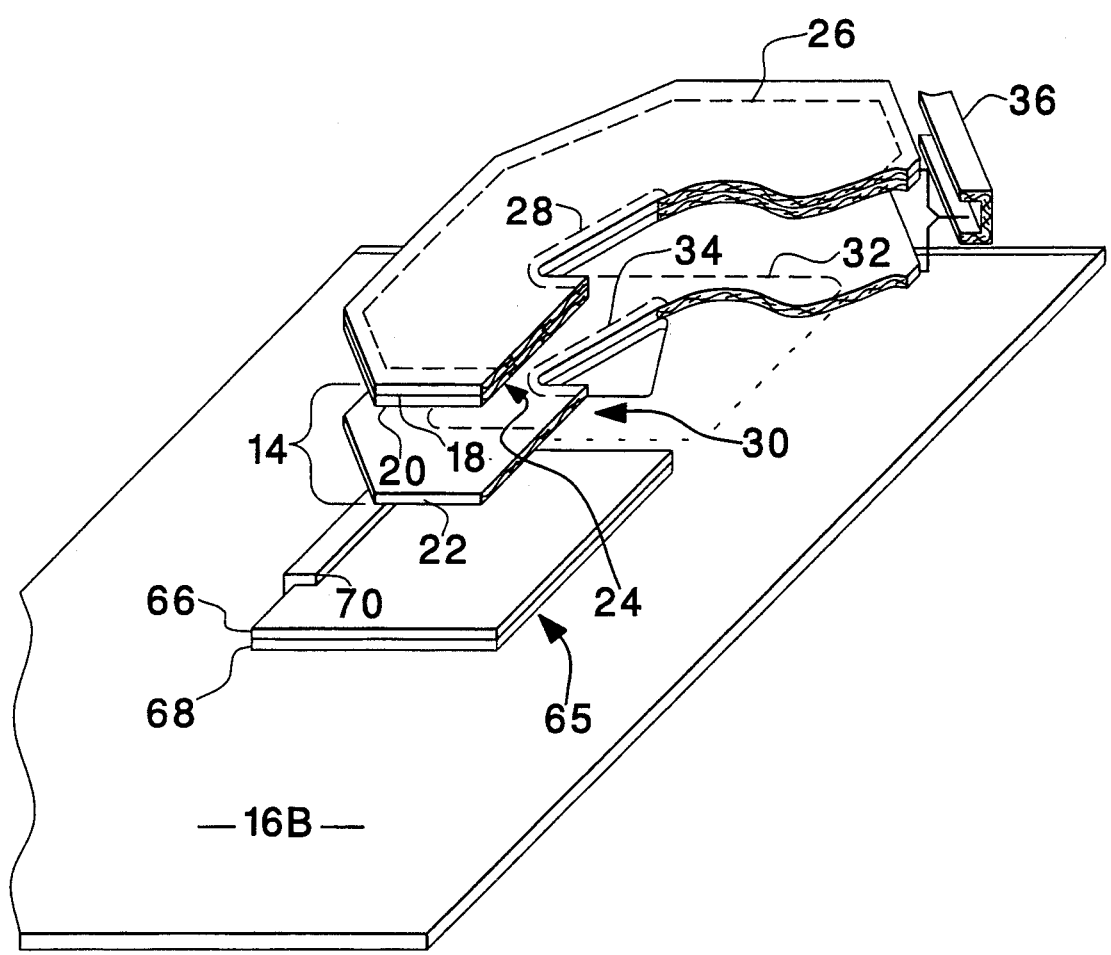
FIG. 5 is a perspective, partially exploded view of subassemblies employed in constructing the present drape.
Figure 6:
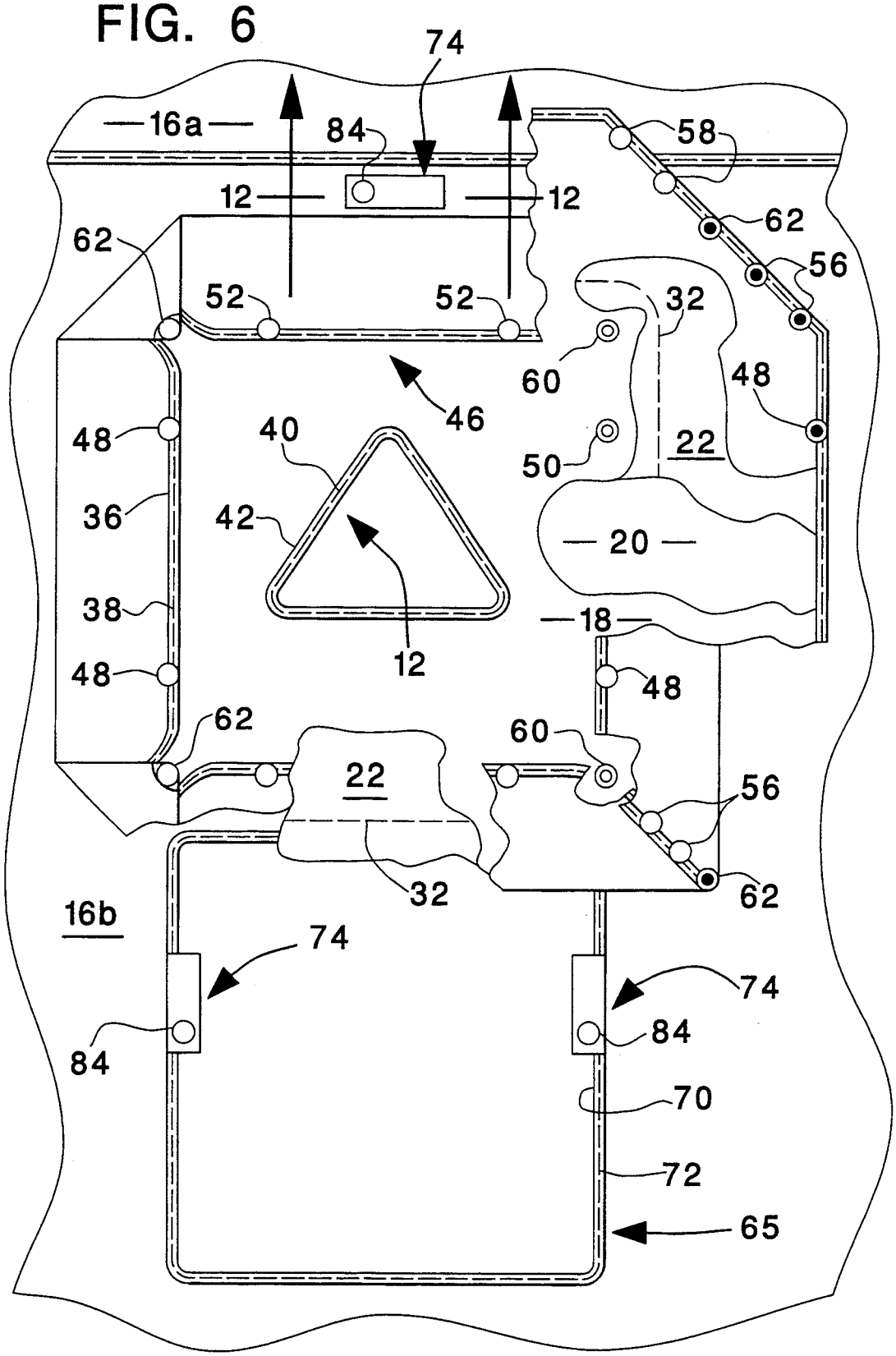
FIG. 6 is a plan view, on an enlarged scale, of a "critical zone" panel employed in the present surgical drape, with portions thereof in various stages of forming troughs.

The "critical zone" panel 14 comprises three washable, fabric panels, namely an upper, absorbent panel 18, an upper barrier panel 20 and a lower barrier panel 22, (FIGS. 2, 5 and 6).

The primary characteristic of the absorbent panel 18 is its ability to absorb liquids. It is further preferred that the panel 18 be non-piling and non-linting after 100 cycles of washing/sterilization. These characteristics may be provided by making the fabric for panel 18 of yarns (knitted or woven), each comprised of a plurality of continuous filaments made of synthetic resinous (plastic) material, preferably polyester, and treating the layer to impart hydrophilic properties thereto. Commercially available hydrophilic finishes may be used to treat the fabric 18 in order to obtain the desired absorbency property.

A further characteristic of the absorbent panel 18 is that it is provided with an irregular surface. This, irregular surface, bordering the fenestration 16, is of great convenience to a surgeon, in that an instrument may be temporarily placed on the "critical zone" panel, with little or no danger of it slipping off the drape. Thus, it is preferred that the absorbent panel 18 have what is referenced, in the textile art, as a texturized surface. Waffle weaves are well known in the textile art and take various forms suitable for the absorbent panel 18, all as will be readily apparent to one skilled in the art. Texturized knit, or woven constructions enhance the absorbency of the panel 18 and, for this further reason, are preferred.

Preferred fabrics for the layer 18 are disclosed, and more particularly described in application for U.S. patent application Ser. No. 548,136, filed Jul. 5, 1990.

As the name implies, the function of the barrier panels 20, 22 is to provide a high resistance to liquid penetration in the "critical zone" marginally of the fenestration 12. Additional characteristics of the barrier panels 20, 22 include flexibility, or a "hand", which permits the "critical zone" portion of the drape to conform to the contour of the patient at the surgical site. Further the panels 20, 22 should be lint free and non-pilling to prevent the introduction of this type of contaminant in the surgical site. Importantly, the fabric for the barrier panels is capable of being repeatedly washed, dried and sterilized using known institutional processes, which employ harsh detergents and involve high temperatures, all without any serious degradation of the noted characteristics.

It has been noted, in prior art teachings, that there is a need for a surgical drape to be "breathable", i.e. to permit the passage of air and/or water vapor therethrough. While there are known barrier fabrics which provide both liquid impermeability and "breathability" one function is, to a greater or lesser extent, inversely proportional to the other. By providing a "critical zone" panel, it is possible to employ barrier fabrics which have increased resistance to liquid penetration, since the main panel 12 provides breathability for the remainder of the drape.

Thus, the fabric for the barrier panels 20, 22 may be selected primarily for its liquid resistant characteristic. A preferred fabric for this purpose is disclosed in U.S. Pat. No. 5,183,702. The referenced fabric is generally characterized by a silicone membrane having a thickness of 0.002–0.010 inches, which is bonded to a tightly woven, polyester fabric substrate. Such fabrics, having a weight in the range of approximately 6–7 ounces per square yard have the desired "hand".

An alternate fabric for the barrier panels 20, 22 is taught in U.S. Pat. No. 4,822,667. That fabric is a tightly woven polyester fabric which is calendared and provided with finish treatments that enable it to have the desired resistance to liquid penetration after as many as 100 washing/sterilization cycles.

Figure 9:
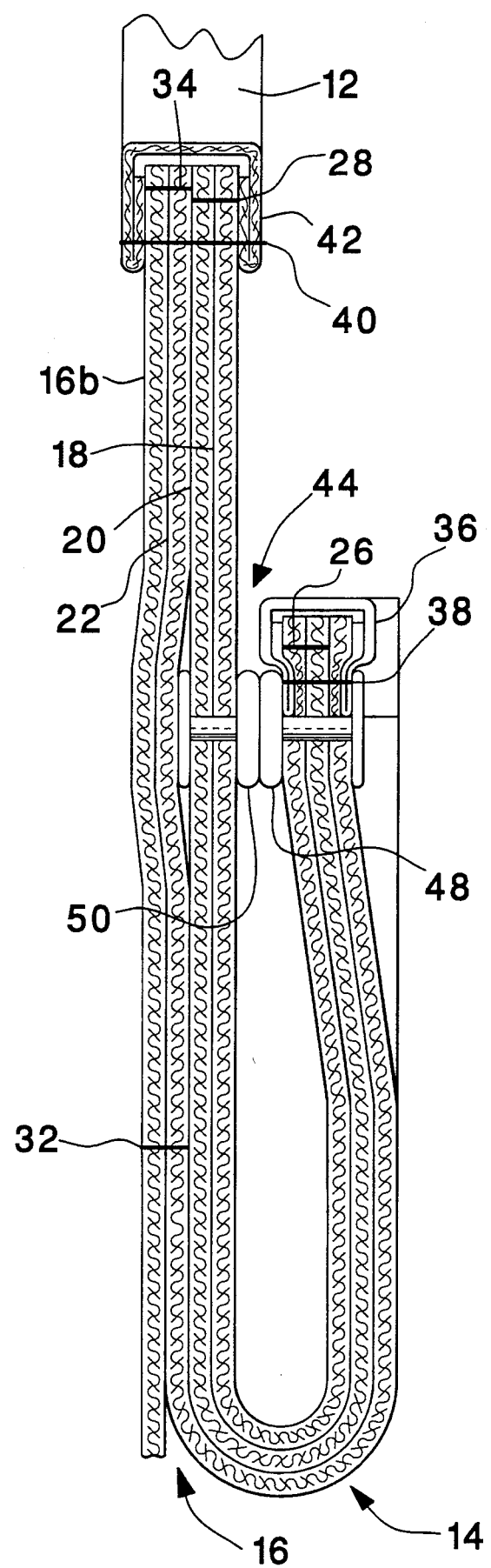
FIG. 9 is a section, on a further enlarged scale, taken on line 9—9 in FIG. 6.
Figure 10:
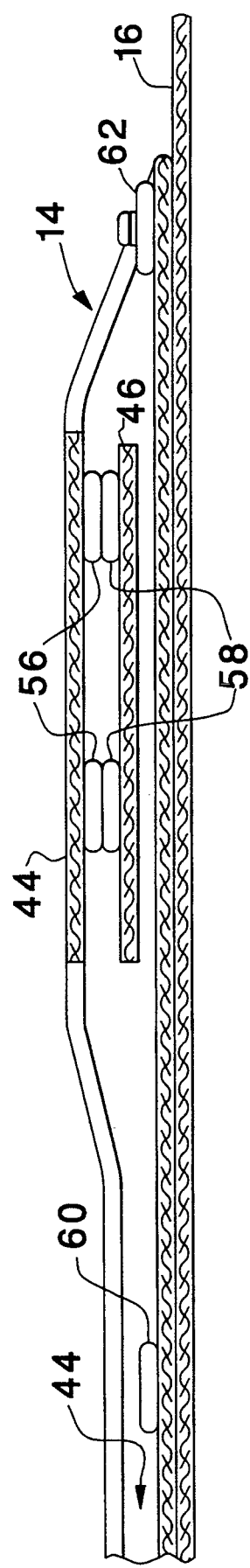
FIG. 10 is a section, on a further enlarged scale, taken on line 10—10 in FIG. 6.

A preferred method of constructing the drape 10 includes joining the panels 18 and 20, to provide a sub-assembly 24. More specifically the panels 18 and 20 are joined by stitching 26 marginally of their outer peripheries, see FIGS. 5 and 9. Also, these panels are joined by stitching 28 marginally of the openings that define the fenestration 12.

The lower barrier 22 is stitched to the main panel 16, more specifically the panel 16b, to form a second sub-assembly 30. This sub-assembly can be made before or after the panels 16a and 16b have been joined, as described above. More specifically the lower barrier panel 22 is joined to the main panel by a rectangular pattern of stitching 32, which is spaced inwardly from the edges of the panel 22. These panels may also be joined by a stitching 34 marginally of the openings for the fenestration 12.

The final assembly step is to join the sub-assemblies 24, 20. This is, likewise, accomplished by stitching. Preferably, a binding tape 36 extends around the registered peripheries of the "critical zone" panels 18, 20 and 20 and is secured in place by marginal stitching 38. Additionally the four panels of the two sub-assemblies are joined by stitching 40, peripherally of the fenestration 12, which secures a binding tape 42, that defines the fenestration 12.

The several stitchings herein are preferably formed with the use of polyester thread to create a stitched seam which has some degree of liquid penetration resistance. It is also possible to provide means for liquid proofing stitched seams. One of the ends achieved by the present invention is to minimize the added expense of waterproof seams, as well as to avoid the necessity of relying on such liquidproof seams as the primary means for maintaining protection against liquid penetration through the main panel 16.

At this point it will be noted that the openings in the several panels, for the fenestration, need not be formed in any particular sequence. One approach would be to form the openings in the several panels before any assembly step is made. Alternatively the openings could be made after joining of the subassemblies 24, 30. Finally, these openings can be formed in the panels by a single die cut, after the sub-assemblies have been joined, or positioned for joining.

A description will next be given of the means whereby troughs are formed on the four side edges of the "critical zone" panel 14. It will first be noted that the outline of the "critical zone" panel 14 is generally rectangular and, in the case if a Cesarian section drape, is preferably square. The corner edges of this square outline are on 45° angles to reduce the bulk of fabric at the corners of the troughs, as will later appear.

It should also be noted, that, for terms of reference, the portions of the "critical zone" panel parallel to lengthwise direction of the operating table are referenced as its sides, and the portions of the "critical zone" panel at right angles thereto are referenced as ends.

In brief, marginal edge portions of the two sides and the two ends of the "critical zone" panel 14 are folded inwardly to form side pockets 44 on opposite sides off the "critical zone" panel and end pockets 46 on opposite ends of the "critical zone" panel.

To this end, upwardly facing, male, snap fastener elements 48 (FIGS. 2 and 6) are mounted in spaced relation along the lengths of the side edges of the "critical zone" panel 14. These snap fastener elements are releasably engageable with upwardly facing, female, snap fastener elements 50 that are mounted on the "critical zone" panel inwardly of the side edges. (In the plan views male snap fastener elements are represented by a solid circle and female snap fastener elements are represented by a central, circular outline.) When the respective fastener elements 48, 50 are engaged (FIGS. 6 and 9) the side troughs 44 are formed.

The end troughs 46 are similarly formed. Thus upwardly facing, male, snap fastener elements 52 (FIGS. 2 and 6) are mounted in spaced relation along the lengths of the end edges of the "critical zone" panel. These snap fastener elements are releasably engageable with upwardly facing, female, snap fastener elements 54 that are mounted on the "critical zone" panel inwardly of the end edges. When the respective fastener elements 52, 54 are engaged (FIGS. 6) the end troughs 46 are formed.

The ends the troughs 44, 46 meet, respectively, at the corners of the "critical zone" panel 14. The ends of the troughs are closed in the manner now to be described.

At each corner there is set of corner forming snap fastening elements. Each set includes a pair of upwardly facing, male snap fastener elements 56 mounted on the angled corner edge of adjacent the side edge of the "critical zone" panel. A pair of downwardly facing snap fastener elements 58 are mounted on the angled corner edge, adjacent the end edge of the "critical zone" panel.

Figure 7:
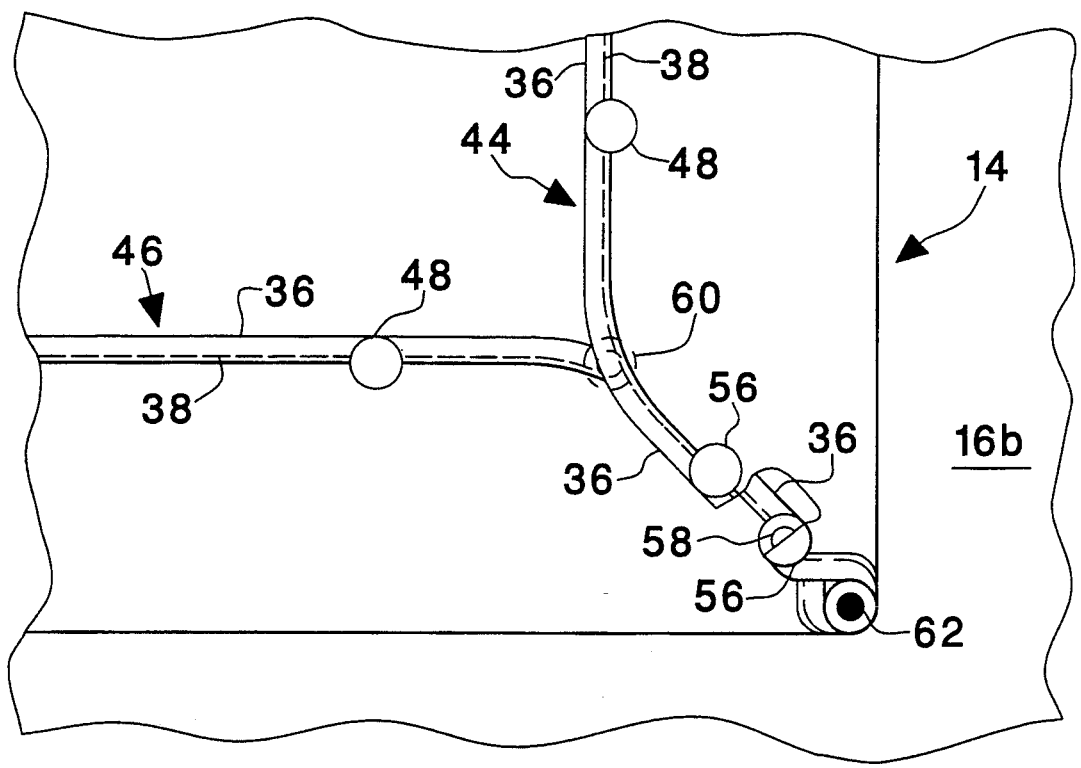
FIG. 7 is a plan view, on a further enlarged scale, of a corner portion of the "critical zone" panel seen in FIG. 6.

In preparing the surgical drape for use, the snap fastener elements 52 may first be engaged with the snap fastener elements 54 to form the end troughs 46. This brings the female snap fastener elements 58 into an upwardly facing position. The side troughs 44 may be formed by engaging the snap fastener elements 48 with the snap fastener elements 50. When this is done, the snap fastener elements 56 may be engaged with the snap fastener elements 58 to partially close the ends of the adjacent ends of the troughs 44 and 46, as is illustrated by the lower right hand corner in FIG. 6 and in FIG. 7.

The set of snap fastener elements at each corner of the "critical zone" panel 14 also includes an upwardly facing, female snap fastener element 60, which is generally positioned at the intersection of the lines on which the snap fastener elements 50 and 54 are mounted. Further, an upwardly facing, male, snap fastener element 62 is mounted on the angled corner edge of the "critical zone" pane 14, intermediate its length.

Figure 11:
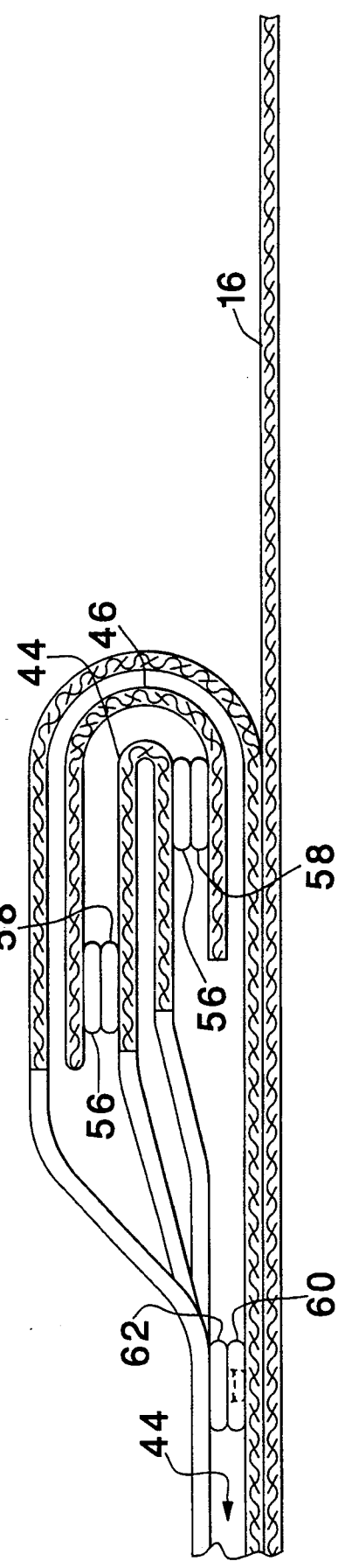
FIG. 11 is a section, on a further enlarged scale, taken on line 11—11 in FIG. 6.

After the snap fastener elements 48, 50 and 52, 54 have been engaged to form the troughs 44, 46 and the snap fastener elements 56, 58 have been engaged, the folded portions of the "critical zone" panel are then folded about a line generally half way between the engaged, snap fastener elements 56, 58. The snap fastener elements 62 may then be engaged with the snap fastener elements 60 to close the adjacent ends of the troughs 44, 46 at each of the four corners of the "critical zone" 14, reference the left hand corners of the "critical zone" panel in FIG. 6 and the corner construction as illustrated in FIG. 11.

When the surgical drape 10 is deployed on a patient, during the performance of a surgical procedure (FIG. 1). The troughs 44, 46 will be angled to a more or less upwardly open position. Thus, liquids incident to the surgical procedure will be prevented from flowing onto the main panel 16. Instead, such liquids will either flow directly into one or the other of the side troughs 44, or flow first to one or the other of the end troughs 46 and then into the side troughs 44.

The entrances to the troughs are defined by the edges of the inwardly folded portions of the "critical zone" panel. These edges are spaced from the underlying portion of the "critical zone" panel so that instruments that are placed on the "critical zone" panel, adjacent the fenestration 12, should they slip, are captured in one or another of the troughs (44, 46) rather than falling to the operating room floor.

The side troughs 44 have a substantial depth so that a substantial volume of liquid can be captured therein. For most procedures, the reservoir capacity of the side troughs is sufficient to hold the total volume of liquids incident to the procedure. This means that operating room personnel do not have to suction, or otherwise remove, liquids from the trough, as a primary function that would interfere with their capability to assist in the procedure being performed. Dependent on time and opportunity available, the troughs 44 need only to be suctioned periodically to prevent liquids from spilling to the floor of the operating room. In many cases, it would be a practice to suction liquid from the troughs 44 only when the procedure is completed and before the drape is removed from the patient.

There are several features of the described construction that have significance, as will now be described.

The described surgical drape facilitates the necessary laundering/sterilization cycle that must be performed after its use to the end that the drape may be safely used in a subsequent surgical procedure. This is to point out the several snap fastener elements may be readily disengaged so that the "critical zone" panel is in a flat, or unfolded condition when it is processed in a washing machine during the laundering process. This unsnapped condition of the "critical zone" panel also facilitates drying of the drape in that there are no crevices that would trap water.

At this point it will be noted that the snap fastener elements are of a well known, commercially available type. Male and female snap fastener element may be readily engaged by forces axial of the elements, this being in a direction at right angles to the plane of the fabric panels to which they are attached. The snap fastener elements are highly resistant to separation in response to forces that would be at right angles to the fastening elements, i.e., in a direction in the plane of the fabric panels.

These characteristics of snap fastener elements prevent inadvertent separation of engaged snap fastener elements that could result in liquid spilling from the troughs 44, or the closed corners thereof. At the same time the snaps can be readily disengaged for laundering of the drape and then easily reengaged prior to sterilization. With the snap fastener elements engaged during sterilization, the surgical drape is immediately ready for use when removed from a sterile package in the operating room.

It is preferred that the male snap fastener elements be facing downward when they are engaged with female, snap fastener elements, as has been herein described. The male, snap fastener elements could, however, be upwardly facing.

Figure 8:
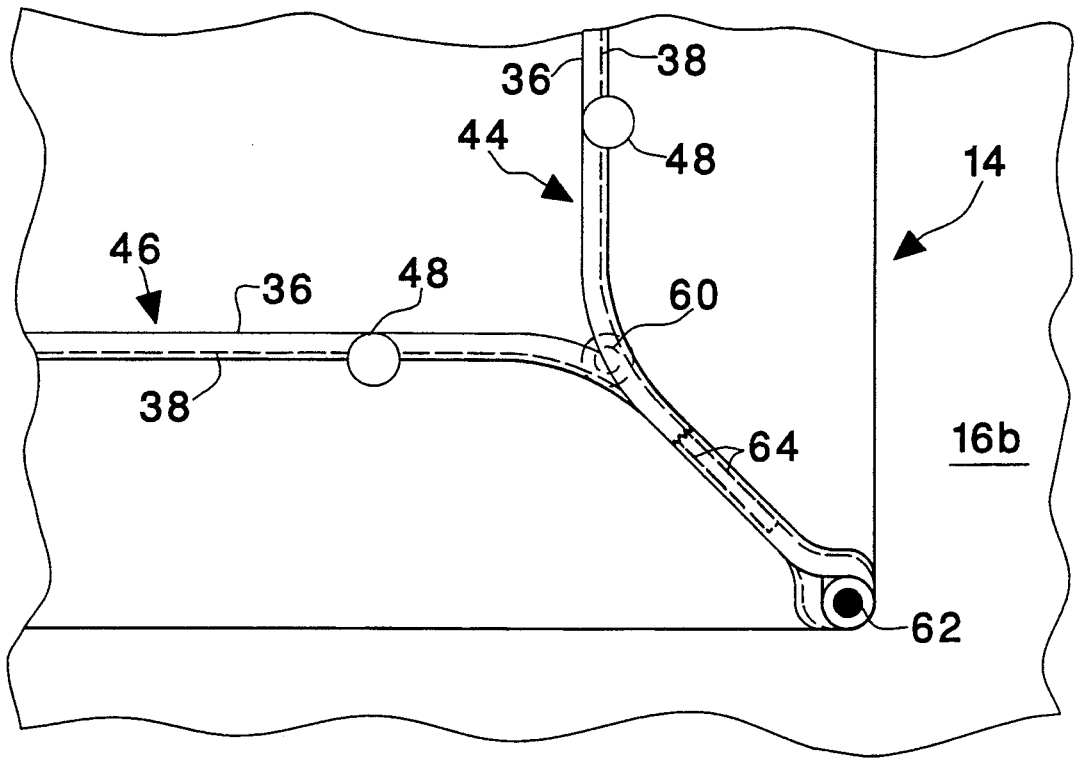
FIG. 8 is a plan view, similar to FIG. 7, illustrating an alternate corner construction for the "critical zone" panel.

FIG. 8 illustrates an alternate corner closing construction which also facilitates the laundering function, with the elimination of two pair of snap fastening elements at each corner of the "critical zone" panel. This is a more economical construction and is more readily opened to a laundering position and then more readily restored to a condition ready for use, after sterilization.

In this alternate corner construction, the overlapping portions of the angled marginal edge portions, at the corner of the "critical zone" panel are joining by stitching 64 rather than by the snap fastener elements 56, 58. It is to be noted that the extreme corners of the troughs 44, 46 remain open, as in the previous construction. With this arrangement, after the drape has been used, the trough forming snaps, 52, 54 and 48, 50 may be disengaged. With these snap fastener elements disengaged, the openings in the corner constructions provide for a sufficient flow of water for the troughs to be effectively laundered.

The surgical drape 10, being adapted for use in the performance of Caesarian sections, is provided with a baby receiving pad 65 which is secured to the main panel 16a immediately below the "critical zone" panel 14 (FIGS. 2 and 5). Upon delivery of a baby, it may be temporarily positioned on the pad 65 until the umbilical cord is severed.

The pad 65 may also be used as an additional working area on which sponges, instruments may be placed for ready access by the surgeon or assistants in the performance of a Caesarian section, or other procedures.

Preferably the pad 65 comprises an upper, absorbent panel 66, having a relatively high coefficient of friction, which characteristics may be attained by using the same fabric as is employed in forming the "critical zone" absorbent panel 18. The pad 65 further comprises a barrier panel 68 which may be formed of the same fabric as is employed in forming the "critical zone" panels 20, 22. The panels 66, 68 may be joined by a marginally sewn binding tape 70 to form the pad 65. The pad 65 may then be secured to the main panel 16a by stitching 72 that extends through the binding tape 70.

When a baby is positioned on the pad 65, it is protected against shifting by the pad 65. At the same time the absorbent upper layer will generally have sufficient capacity to prevent liquids from spilling onto the floor and the barrier panel will prevent liquid from striking through the main panel 16 to contact the patient.

It is to be noted that the construction of the present surgical drape maximizes "critical zone" protection. This end is achieved through the provision of the two barrier panels 20, 22 in the "critical zone" panel 14. The achievement of such end is further enhanced by the fact that there is no stitched connection, or other interconnection, between the upper barrier panel 20 and the main panel 16, other than that immediately adjacent the fenestration 12. Attainment of this end is further facilitated by the method aspects of the invention.

As previously indicated, the lower barrier panel 22 is separately fastened to the main panel 16. This end is achieved through the stitching 34, marginally of the fenestration 12, and the stitching 32. At this point, it will be noted that the stitching 32 is parallel with the adjacent side or end edge of the "critical zone" panel 14 (after assembly). It is also to be noted that the respective stitchings 32 are intermediate the heights of the troughs 44, 46 (FIG. 9) and, preferably, are approximately at the midpoint of the heights of these troughs. This relative position of the stitchings 32 minimizes the lengths of the marginal portions of the "critical zone" panel 32 which are free to flap during washing and drying of the drapes. By minimizing such flapping, the abuse and stress on the panels and stitching is minimized and the service life of the drape increased.

It is further to be noted that the snap fastener elements 50, 54 and 60 are secured only to the upper barrier panel 20 and absorbent panel 18. Preferably this is done after these panels have been joined to form the sub-assembly 24. Then, after the sub-assembly 24 has been joined to the sub-assembly 30, the snap fastener elements 48, 52, 56, 58 and 62 are secured to all three panels (18, 20 and 22) of the "critical zone" panel 14.

The upper barrier panel 20 is essentially repellant to liquid penetration, particularly when formed of fabric as taught in the referenced 5,183,702 patent. Nonetheless, it is possible that a leak in this panel could result from abuse occurring during its use. The second, underlying barrier panel thus serves as a backup to provide liquid strikethrough protection in the "critical zone" should the barrier property of the upper panel 20, be compromised.

It is to be noted that any penetration of a barrier fabric panel creates the potential for a strikethrough. With the present construction, the only penetration of the upper barrier 20, which is in communication with the main panel 16 is at the stitching 40, marginally of the fenestration 12.

The snap fastener elements, which penetrate and are riveted in place, as described, also create the potential for a strikethrough, particularly after several laundering cycles, which would involve stresses that would tend to tear the fabric. By securing the snap fastener elements 50, 54 and 60 only to the sub-assembly 24, should a leakage flow path develop at any of these snap fastener elements, the underlying, second barrier panel 22, serves as a backup to minimize, if not completely eliminate, the possibility of there being a strikethrough in the "critical zone" panel. The remaining snap fastener elements penetrate the second "critical zone", but, in use, are disposed outwardly of the main panel so that, in the unlikely event of a leakage, there would be no strikethrough in the main panel.

The broader advantages of the present invention can also be attained in a surgical drape in which the absorbent panel 18 is omitted. In such case, what has been referenced as sub-assembly 24, would simply be comprised of the upper barrier panel 20.

It is also to be appreciated that, in accordance with the broader aspects of the invention, the benefits of employing an upper and a lower barrier panel in a "critical zone" panel can be attained in surgical drape constructions, which have troughs only at the sides of the "critical zone" panel, as taught in the above referenced parent application Ser. No. 680,089, as well as in a copending application filed contemporaneously with present invention and which is of common assignment.

Also, in accordance with other of the broader aspects of the present invention, it may well be sufficient to provide only one end edge trough 46. If only a single trough 46 were provided, it would, most likely, be the one between the fenestration 12 and the pad 65.

A further feature of the present invention is found in tube loops 74. Tube loops are a known means for holding electrical instruments during its use in a surgical procedure. The tube loops 74, now to be described are adapted to clamp elongated instruments having a diameter approximating that of a pencil. The tube loops 74 may be positioned at various locations on the drape 10. For sake of illustration one tube loop 74 is mounted at the upper end of the "critical zone" panel 14 and two tube loops 74 are mounted, respectively, on opposite sides of the pad 65 (FIG. 6).

Figure 13:
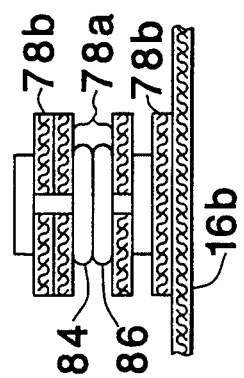
FIG. 13 is a section, taken on line 13—13 in FIG. 12.
Figure 12:
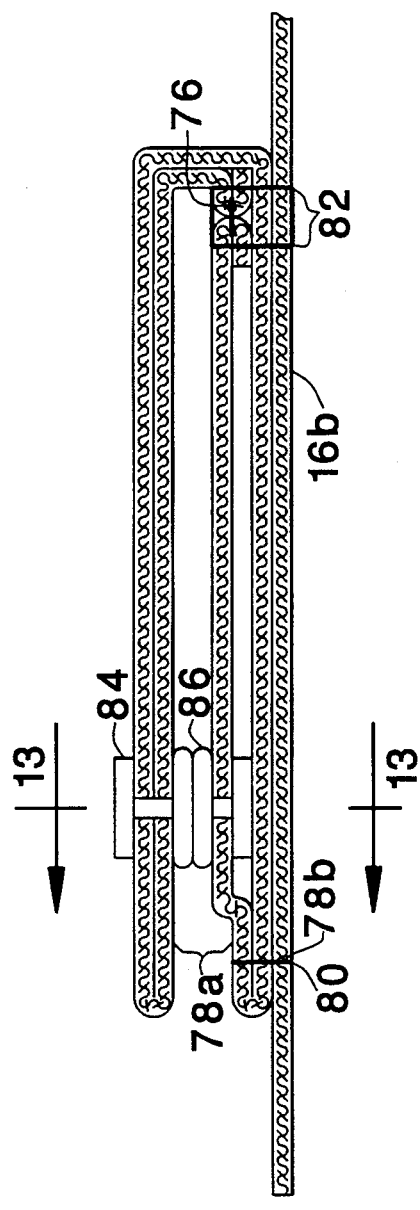
FIG. 12 is a section, on a greatly enlarged scale, taken on line 12—12 in FIG. 6, illustrating a tube loop of the present invention.
Figure 14:
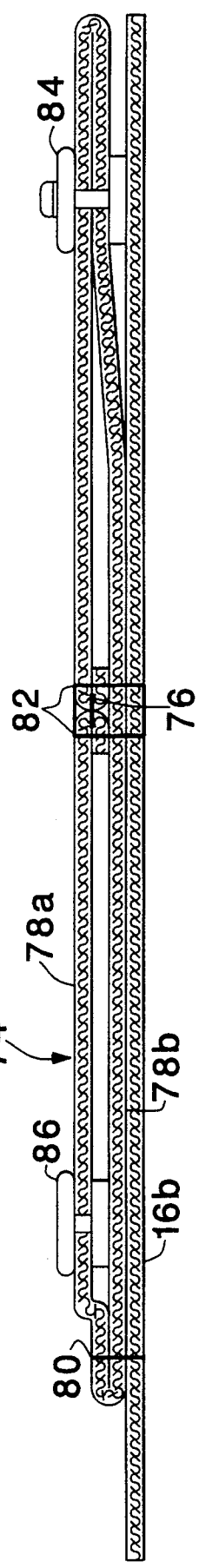
FIG. 14 is a section, similar to FIG. 12, illustrating the tube loop in an unfastened position.

Each tube loop 74 (FIGS. 12-14) is formed of a length of twill, or other woven fabric tape, which is also launderable, consistent with the end of providing a reusable surgical drape. The length of twill tape, which may have a width in the order of ⅜ inch, is formed into an endless loop by stitching 76. The marginal end portions of the tape are folded in opposite directions, with the stitched side of the loop (best seen in FIG. 14) facing upwardly, as the loop is flattened against the main panel 16b to form a two ply strap, the upper strap ply being identified by reference character 78a and the lower strap ply being identified by reference character 78b. The stitching 76 is disposed approximately at the center of the upper strap ply 78a.

Approximately half of this loop formed strap is secured to the main panel 16b by stitchings 80, 82, which extend across the width the tape strap. The stitching 80 extends through the plies 78a and 78b and is disposed adjacent the end of the strap. The stitching 82 is disposed approximately at the midpoint of the flattened, tape loop and also extends through both of the plies 78a and 78b. The stitching 82 may be in the form of a bar tack which has a width such that stitching goes through the ply 78a on opposite sides of the connecting stitching 76.

A male snap fastener element 84 is mounted on the free end of the tube loop strap (to the right of stitching 82) by clamping it onto both of the plies 78a, 78b at that end. A female snap fastener element 86 is mounted on the fixed portion of the tube loop strap by clamping it onto only the upper loop ply 78a.

When the snap fastener element 84 is engaged in the snap fastener element 86, a closed loop is formed. An electrical instrument would be captured within this closed loop to hold it in place during its use.

The significant factor to be recognized, in connection with the described tube loop 74 is that it inherently provides at least one layer of fabric between the metallic snap fastener and the patient. Actually, in all but the most exceptional of cases, there would be at least two layers of fabric serving to insulate the patient from contact with the metal snap fastener element.

This is to point out that the snap fastener element 86 (which could, as well, be a male snap fastener element) is mounted only onto the upper loop ply 78a. Thus, when the loop is mounted on the drape, the loop ply 78b will be disposed between the snap fastener element 86 and the underlying patient. Further, the strap formed by the plies 78a, 78b, when attached to the drape disposes the snap fastener element 86 so that the drape fabric (main panel 16b in the case of the described tube loop) is also disposed between the snap fastener element 86 and the patient. The snap fastener element 86 is thus further spaced from and insulated from the patient.

With this arrangement, should there be some malfunction, which results in the casing of the electrical instrument being electrically charged and, should that casing come into contact with any portion of the snap fastener elements 84, 86, the patient will be protected from an electrical shock and/or burn by the lower ply 78b and any intact, fabric layers of the drape, that are disposed between the tube loop and the patient.

It is to be appreciated that the tube loop could be readily modified to accommodate instruments of different diameters. This could be done by extending the length of the free end of the two plied strap and then mounting a plurality of male fasteners 84 along the length or this free end. A given fastener 84 could then be selected to engage the snap fastener element 86 to form a loop of appropriate size to hold a given instrument.

Alternatively, the same end could be attained by extending the length of the fixed portion of the tube loop strap and then mounting a plurality of fasteners along its length for selective engagement by the snap fastener on the free end of the tube loop strap.

The discussed variations in construction and other departures from the embodiments described will occur to those skilled in the art within the spirit and scope of the present inventive concepts, which are defined in the following claims.

Having thus described the invention, what is novel and desired to be secured by Letters Patent of the United States is:

1. A reusable, surgical drape adapted to overlie a patient during the performance of a surgical procedure and having a fenestration for registration with the site of a surgical procedure,
   said drape being constructed of launderable/sterilizable fabric panels, comprising
   a main panel of a given lateral extent,
   a "critical zone" panel
      having a substantially smaller, lateral extent, and
      extending outwardly from said fenestration,
   wherein
   a marginal edge portion of the "critical zone" panel is
      folded on itself to define a bottom, folded portion,
   said marginal edge portion being in spaced relation to
      the main portion of the "critical zone" panel and
      forming an upwardly open, trough extending upwardly from the bottom, folded portion, for the
      reception therein of liquids incident to the performance of a surgical procedure, and
   including releasable means for securing said folded
      portion of the "critical zone" panel to said main
      portion so that the folded portion may be released
      to facilitate washing of the drape,
   characterized in that
   the "critical zone" panel comprises
      an upper barrier panel, and
      a lower barrier panel, and
   the upper barrier panel is joined to the main panel
      only by stitching marginally of the fenestration,
      and
   the upper barrier panel is joined to the lower barrier
      panel by stitching marginally of their outer peripheries.

2. A reusable, surgical drape as in claim 1 wherein snap fastener elements
   provide the releasable securing means and comprise
      first snap fastener elements spaced along an outer
         edge of the "critical zone" panel and
      second snap fastener elements spaced inwardly
         therefrom, and
   further characterized in that the second snap fastener elements are mounted on the upper barrier panel, and are not connected to the lower barrier panel, to the end that the barrier properties of the lower barrier panel are not compromised by mounting the second snap fastener elements thereon.

3. A reusable, surgical drape as in claim 2 further characterized in that
the first snap fastener elements are mounted on both the upper and lower barrier panels.

4. A reusable, surgical drape as in claim 3 further characterized in that
the lower barrier panel is joined to both the main panel and the upper barrier panel by stitching marginally of the fenestration,
the lower barrier panel is joined to the upper barrier panel by stitching marginally of said inwardly folded edge, and
the lower barrier panel is joined to the main panel by stitching parallel to said marginal edge and intermediate the second snap fastener elements and the bottom of said trough.

5. A reusable, surgical drape as in claim 4 further characterized in that
the "critical zone" panel comprises
an absorbent panel disposed in overlying relation to the upper barrier panel, and
the fenestration is defined by a first, binding tape embracing the "critical zone" panel and the main panel,
the binding tape is secured by stitching which provides the means for joining the "critical zone" panel and the main panel and
a second, binding tape is secured by stitching along the outer margins of the first and second barrier panel and the absorbent panel to provide means for joining said panels.

6. A reusable, surgical drape as in claim 1 wherein
the folded marginal edge portion is a side edge portion that provides a trough at one side of the "critical zone" panel, and
further characterized in that
a second marginal edge portion of the "critical zone" panel along one end thereof is folded on itself to define a second, bottom, folded portion, said second marginal edge portion also being in spaced relation to the main portion of the "critical zone" panel to form a second, upwardly open, non-filled trough of substantial depth, for the reception of liquids incident to the performance of a surgical procedure,
said second folded portion of the "critical zone" panel is releasably secured to said main portion so that that folded portion may be released to facilitate washing of the drape, and
said first and second troughs intersect at a corner of the "critical zone" panel, and
further characterized by releasable means for holding the first and second, inwardly folded portions in a further folded relation in which the ends of the troughs, at their intersection, are closed.

7. A reusable, surgical drape as in claim 6 further characterized in that
the first and second inwardly folded portions overlap at the corner intersection, and
further characterized by
means for joining said overlapped portions in a manner providing an opening at said corner, through which liquids may flow to facilitate laundering and sterilization of the drape.

8. A reusable, surgical drape as in claim 7 further characterized in that
the means for joining said overlapped portions comprises stitching.

9. A reusable, surgical drape as in claim 7 further characterized in that
the means for joining said overlapped portions comprises releasable snap fastener means,
whereby the corner portion of the "critical zone" may be put in an unfolded condition by releasing the snap fastener means and thereby further facilitating laundering of the drape.

10. A reusable, surgical drape as in claim 6 further characterized in that
the portion of the "critical zone" panel, which forms the intersecting side and end troughs, in its unfolded condition, is defined by portions of a side edge and a portion of an end edge of the "critical zone" panel disposed at right angles to each other and an interconnecting, angled edge, disposed at a 45° to the side and end edges, and
a first snap fastener element, facing upwardly, is mounted at the midpoint of said angled edge and
a second snap fastener element, facing upwardly, is mounted in the "critical zone" panel, inwardly from said first snap fastener element and at right angles to said angled edge,
said first and second snap fastener elements being engageable to provide the releasable means for holding the first and second, inwardly folded portions in a further folded relation in which the ends of the troughs, at their intersection, are closed.

11. A reusable, surgical drape as in claim 10 further characterized in that
a third snap fastener element, facing upwardly, is mounted on the angled edge on one side of the first snap fastener element, and
a fourth snap fastener element, facing downwardly, is mounted on the angled edge, on the opposite side of the first snap fastener element,
said third and fourth snap fastener elements being engageable, when the side and end marginal edge portions are folded to their trough forming positions.

12. A reusable, surgical drape adapted to overlie a patient during the performance of a surgical procedure and having a fenestration for registration with the site of a surgical procedure,
said drape being constructed of launderable/sterilizable fabric panels comprising
a main panel of a given lateral extent,
a "critical zone" panel
having a substantially smaller, lateral extent, and extending outwardly from said fenestration,
the "critical zone" panel comprises
an upper barrier panel, and
a lower barrier panel, and
the upper barrier panel is joined to the main panel only by stitching marginally of the fenestration, and
the upper barrier panel is joined to the lower barrier panel by stitching marginally of their outer peripheries,
wherein
said "critical zone" panel, in an unfolded condition has a rectangular outline comprising side edges and end edges, disposed at right angles to each other at the corners thereof, and angled edges at the corners angled at 45° to the adjacent side and end edges, marginal side edge portions, on opposed sides of the "critical zone" panel are folded on themselves to define bottom, folded portions, said marginal side edge portions being in spaced relation to the main portion of the "critical zone" panel and forming upwardly open, side troughs, extending upwardly from the bottom, folded portion, for the reception therein of liquids incident to the performance of a surgical procedure, and marginal end edge portions of the "critical zone" panel are folded on themselves to define bottom, folded portions, said end marginal edge portions being in spaced relation to the main portion of the "critical zone" panel and forming an upwardly open, end trough, extending upwardly from the bottom, folded portion, for the reception therein of liquids incident to the performance of a surgical procedure, said end trough, at its opposite ends intersecting with the side troughs, at the corners of the "critical zone" panel, and releasable means for securing the folded portions of the "critical zone" panel to the underlying portions thereof, said releasable means comprising snap fastener elements mounted on the side edges and said end edge of the "critical zone" panel and cooperating snap fastener elements mounted inwardly therein and secured to the upper barrier panel, but not to the lower barrier panel.

13. A reusable, surgical drape as in claim 12 wherein the "critical zone" panel further comprises an absorbent panel forming the top surface of the "critical zone" panel, the component panels of the "critical zone" panel and the main panel have aligned fenestration defining openings, and a binding tape is secured around said openings by stitching that extends through the component panels of the "critical zone" panel and through the main panel, to join all of these panels marginally of the fenestration, and the barrier panels and the absorbent panel of the "critical zone" panel are joined by stitching that secures a binding tape around the periphery of the "critical zone" panel.

14. A reusable, surgical drape adapted to overlie a patient during the performance of a surgical procedure and having a fenestration for registration with the site of a surgical procedure, said drape being constructed of launderable/sterilizable fabric panels comprising a main panel of a given lateral extent, a "critical zone" panel of substantially smaller lateral extent and extending outwardly from said fenestration, wherein the "critical zone" panel comprises a liquid repellant, barrier panel, and a side marginal edge portion of the barrier panel is folded on itself to define a bottom, folded portion, said marginal edge portion being in spaced relation to the main portion of the barrier panel and forming an upwardly open, side trough of substantial depth, extending upwardly from the bottom folded portion, for the reception therein of liquids incident to the performance of a surgical procedure, and an end marginal edge portion of the barrier panel is folded on itself to define an end bottom, folded portion, said marginal edge portion being in spaced relation to the main portion of the barrier panel and forming an upwardly open, end trough, extending upwardly from the bottom folded portion, for the reception therein of liquids incident to the performance of a surgical procedure, said end and side troughs intersecting at a corner of the "critical zone" panel, means for releasably securing said folded, marginal edge portions of the barrier panel to the main portion of the barrier panel, and further characterized by releasable means for securing the folded side and end marginal edge portions, at said corner, in further folded relation that closes the intersecting ends of said troughs.

15. A reusable, surgical drape as in claim 14 wherein snap fastener elements provide the releasable fastening means and comprise first snap fastener elements spaced along adjacent side and end edges and second snap fastener elements spaced inwardly therefrom.

16. A reusable, surgical drape as in claim 15 the snap fastener elements for the side edge of the "critical zone" panel provide means for spacing the edge of the said marginal edge portions from the main portion of the barrier panel, to define a spaced opening for said side trough, which trough is non-filled, thereby facilitating the capture of instruments, or the like, that might slip from a position adjacent the fenestration, thus minimizing the possibility of instruments falling to the floor of the operating room.

17. A reusable, surgical drape as in claim 15 wherein the side and end folded portions overlap at the corner intersection, and further characterized by means joining said overlapped portions in a manner providing an opening, at said corner, through which liquids may flow to facilitate laundering and sterilization of the drape.

18. A reusable, surgical drape as in claim 17 further characterized in that the means joining said overlapped portions comprises stitching.

19. A reusable, surgical drape as in claim 17 further characterized in that the means joining said overlapped portions comprises releasable snap fastener means, whereby the corner portion of the "critical zone" may be put in an unfolded condition by releasing the snap fastener means to thereby further facilitate laundering of the drape.

20. A reusable, surgical drape as in claim 14 further characterized in that the portion of the "critical zone" panel, which forms the intersecting side and end troughs, in its unfolded condition, is defined by portions of a side edge and a portion of an end edge of the "critical zone" panel disposed at right angles to each other and an interconnecting, angled edge, disposed at a 45° angle to the side and end edges, and a first snap fastener element, facing upwardly, is mounted at the midpoint of said angled edge and a second snap fastener element, facing upwardly, is mounted in the "critical zone" panel, inwardly from said first snap fastener element and at right angles to said angled edge, said first and second snap fastener elements being engageable to provide the releasable means for holding the first and second, inwardly folded portions in a further folded relation in which the ends of the troughs, at their intersection, are closed.

21. A reusable, surgical drape as in claim 20 further characterized in that a third snap fastener element, facing upwardly, is mounted on the angled edge on one side of the first snap fastener element, and a fourth snap fastener element, facing downwardly, is mounted on the angled edge, on the opposite side of the first snap fastener element, said third and fourth snap fastener elements being engageable, when the side and end marginal edge portions are folded to their trough forming positions.

22. A method of constructing a reusable, surgical drape adapted to overlie a patient during the performance of a surgical procedure and having a fenestration for registration with the site of a surgical procedure, wherein the surgical drape comprises a plurality of launderable/sterilizable fabric panels, including a main panel of a given lateral extent, a "critical zone" panel having a substantially smaller, lateral extent, and extending outwardly from said fenestration, and the "critical zone" panel comprises an upper barrier panel, and a lower barrier panel, said method comprising the steps of joining the upper and lower barrier panels and the main panel by stitching marginally of the fenestration and joining the outer edges of the upper and lower barrier panel by stitching marginally thereof.

23. A method of constructing a reusable, surgical drape as in claim 22 comprising the further steps of mounting first snap fastener elements inwardly of a given edge of the upper barrier panel prior to the given outer edge being joined to the lower barrier panel, and mounting second snap fastener elements along said given edge in both the upper and lower barrier panels, to thereby provide releasable means for securing the portion of the "critical zone" panel, marginally of said given edge, in a folded, trough defining position.

24. A method of constructing a reusable, surgical drape as in claim 23 wherein the "critical zone" panel further includes an upper, absorbent panel, and comprising the further steps of joining the absorbent panel and the upper barrier panel to form a first sub-assembly, prior to mounting said first snap fastener elements, said first snap fastener element elements are mounted in both the absorbent panel and the upper barrier panel, the lower barrier panel is joined to the main panel by stitching marginally of the fenestration to form a second sub-assembly, and then joining the two sub-assemblies, and then joining the first sub-assembly to the lower barrier panel by stitching marginally of their outer edges.

25. A method of constructing a reusable, surgical drape as in claim 24 comprising the further step of joining the lower barrier panel to the main panel by stitching parallel to said given edge and intermediate said edge and said first snap fastener elements, prior to joining the outer edge of the lower barrier panel to the first sub-assembly.

26. A method of constructing a reusable, surgical drape as in claim 25 wherein the step of joining the two sub-assemblies includes stitching binding tape around the periphery of the fenestration, and the step of joining the lower barrier panel to the first sub-assembly includes stitching binding tape around the outer periphery of the "critical zone" panel.

27. A reusable, surgical drape adapted to overlie a patient during the performance of a surgical procedure in which an electrical instrument is to be employed, wherein the drape includes a tube loop for releasably holding the electrical instrument, said tube loop comprising an endless loop formed of fabric, said fabric loop being flattened to form a strap comprised of an upper fabric ply and a lower fabric ply, means for securing one end portion of the strap to the drape, leaving the remainder of the strap as a free end portion, a first, metallic snap fastener element mounted on the free end portion of the strap, a second, metallic snap fastener element mounted on the secured end portion of the strap and adapted to be engaged by the first snap fastener element in holding an electrical instrument, characterized in that the second snap fastener element is mounted onto the upper fabric ply and the lower fabric ply is disposed between the second snap fastener element and the drape to thereby space the snap fastener elements from a patient upon whom the drape has been positioned and thus protect the patient from an electrical shock and/or burn.

28. A reusable, surgical drape as in claim 27, further characterized in that the first snap fastener element is mounted onto both the upper and lower plies of said strap.

29. A reusable, surgical drape as in claim 28, further characterized in that the endless fabric loop is formed of a length of woven tape, the ends of which are joined by a first stitching, the joined ends of the length of tape are disposed in the upper ply of the strap, and the means for securing one end portion of said strap to the surgical drape comprise second stitching disposed between the second snap fastener element and the outer end of the secured portion of the strap, and third stitching disposed intermediate the length of said strap.

30. A reusable, surgical drape as in claim 29, further characterized in that the first stitching is disposed approximately at the midpoint of the length of said strap, the end portions of the loop, outwardly of the first stitching are reversely folded, in opposite directions, to underlie the upper ply of the strap, and the third stitching is also disposed approximately at the midpoint of the length of said strap.

31. A reusable, surgical drape as in claim 30, further characterized in that the endless loop is formed of twill tape, the first snap fastener element is a male snap fastener element, the second snap fastener element is a female snap fastener element, and the third stitching is a bar tack, which provides stitching on opposite sides of said first stitching.

* * * * *